United States Patent [19]

Breitzke

[11] Patent Number: 4,871,777

[45] Date of Patent: Oct. 3, 1989

[54] EMULSIFYING COMPOSITIONS FOR SUPPOSITORY BASES AND SUPPOSITORIES PRODUCED THEREFROM

[75] Inventor: Willi Breitzke, Duesseldorf, Fed. Rep. of Germany

[73] Assignee: Henkel Kommanditgesellschaft auf Aktien, Duesseldorf, Fed. Rep. of Germany

[21] Appl. No.: 173,348

[22] Filed: Mar. 24, 1988

[30] Foreign Application Priority Data

Mar. 25, 1987 [DE] Fed. Rep. of Germany ....... 3709861

[51] Int. Cl.$^4$ .............................................. A61K 9/02
[52] U.S. Cl. ................................... 514/785; 514/966; 514/969; 424/502; 424/DIG. 15; 604/288
[58] Field of Search ...................... 514/966, 969, 785; 604/288; 424/DIG. 15, 502

[56] References Cited

U.S. PATENT DOCUMENTS 4,368,185 1/1983 Mizuno et al. ............. 424/DIG. 15

FOREIGN PATENT DOCUMENTS 0082760 11/1979 Luxembourg .

OTHER PUBLICATIONS

Chem. Abstract 95:30401k.
Chem. Abstract 88:158485p.
Chem. Abstract 98:221748a.
Chem. Abstract 105:48957f.
Suppositorien by Prof. Dr. Bernd. W. Muller, 1986, pp. 94–101, DAB 9, 1986.
Europäisches Arzneibuch by Prof. Dr. Dr. h.c. H. Böhme and Prof. Dr. K. Hartke, pp. 248–252.

*Primary Examiner*—John Kight
*Assistant Examiner*—Nathan M. Nutter
*Attorney, Agent, or Firm*—Ernest G. Szoke; Wayne C. Jaeschke; Norvell E. Wisdom

[57] ABSTRACT

A composition for suppository bases consisting of a water-insoluble fat and an adduct of 5 to 50 mol ethylene oxide with 1 mol hardened castor oil as emulsifier enables suppositories containing aqueous active-principle solutions to be prepared. The emulsifier is preferably present in a quantity of 0.2 to 10% by weight. Suppositories containing up to 30% by weight water dispersed therein can be prepared using the above composition.

12 Claims, No Drawings

EMULSIFYING COMPOSITIONS FOR SUPPOSITORY BASES AND SUPPOSITORIES PRODUCED THEREFROM

BACKGROUND OF THE INVENTION

1. Field of the Invention

This invention relates to compositions for suppository bases having a good emulsifying effect for water, aqueous active-principle solutions, and polar active principles.

2. Statement of Related Art

Suppositories are cylindrical or slightly oval plugs of a composition fusible at body temperature in which medicaments are dissolved, dispersed or emulsified and which are intended for the application of those medicaments in the rectum of human beings.

Accordingly, suppositories consist essentially of a suppository base and active principles. The suppository base may contain certain auxiliaries which improve the viscosity, processability and stability of the base and the suppositories produced therefrom or which serve to improve the distribution of the active principles in suppositories and the adsorption of the active principles in the rectum. Water-insoluble fats are largely used as suppository bases. However, water-soluble compositions based on polyethylene glycols are also known, although they are of only limited importance due to their incompatibility with many active principles, their hygroscopicity and the resulting irritant effect on mucous membrane, and their tendency towards subsequent hardening. Finally, water-dispersible compositions based on certain nonionic surface-active ethylene oxide adducts are also known, although they have not acquired any commercial significance for similar reasons. However, a certain significance has been acquired by the so-called "hydrophilic fat bases", i.e. mixtures of lipophilic fats and certain nonionic emulsifiers.

However, known suppository bases based on lipophilic fats and also known "hydrophilic" suppository bases are unsuitable for the problem-free and stable incorporation of aqueous active-principle preparations or highly polar active principles, such as for example phenols, glycerol, sugar, in the often very large quantities required. Instead, separation frequently occurs in the cast suppositories. As a result, inhomogeneous, friable or fragile suppositories are obtained, giving rise to considerable problems in production and in use.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, an object of the present invention is to provide compositions for suppository bases based on water-insoluble fats in which even dilute aqueous solutions or dispersions of certain active principles and other highly polar components, such as for example glycerol, phenols, salts, for example of shale oil sulfonic acids (Ichthyol ®) may be homogeneously and stably incorporated without difficulty in relatively large quantities by emulsification.

According to the invention, this object is achieved by compositions for suppository bases consisting of a water-insoluble fat and an emulsifier, wherein an adduct of 5 to 50 mols of ethylene oxide with 1 mol of hardened castor oil is present as the emulsifier.

In the context of the invention, water-insoluble fats are understood to be fats of the type defined in detail in the book entitled "Suppositorien" by Prof. Dr. Bernd. W. Muller (Wissenschaftliche Verlagsgesellschaft mbH, Stuttgart, 1986), Chapter 2.2.4.2, pages 94–101. These fats include cocoa butter, hardened vegetable oils and, especially, mixtures of mono-, di- and triglycerides of saturated fatty acids $C_{10}H_{20}O_2$ to $C_{18}H_{36}O_2$, which correspond to the specification in DAB 9 (1986) and in the Europaisches Arzneibuch fur Hartfett (Adeps solidus). In exceptional cases, fatty acid esters of monohydric alcohols (waxes) and dihydric alcohols (for example 1,2-propylene glycol dimyristate or palmitate), branched fatty alcohols (Guerbet alcohols containing 32 to 40 carbon atoms) or dicetylphthalate can be used herein as the water-insoluble fats for supppository bases. However, glycerol fatty acid esters (mono-, di- and triglycerides) are preferred. They are prepared either from hardened natural fats, for example coconut oil or palm kernel oil, by transesterification with glycerol and, optionally, fatty acids having a different C chain distribution to adjust the required characteristic values (acid value and hydroxyl value) and the desired melting behavior. However, suitable fatty acid cuts, preferably containing 10 to 18 carbon atoms, can also be directly esterified with glycerol.

The adduct of 5 to 50 mols of ethylene oxide with 1 mol of hardened castor oil suitable for use as the emulsifier is prepared by ethoxylation of hardened castor oil under conditions known per se, i.e. the hardened castor oil is reacted with the calculated quantity of ethylene oxide at 140° to 200° C. in the presence of a basic catalyst, such as for example sodium methylate of potassium hydroxide.

The compositions of the invention for suppository bases contain from 0.1 to 20% by weight of the above emulsifier. In addition, the compositions of the invention for suppository bases can contain relatively small quantities, for example up to a total of 5% by weight, of other known auxiliaries for regulating the melting behavior, viscosity and processibility of the suppository base and for improving the appearance of the suppository base or of the suppositories produced therefrom, which include for example beeswax, cetostearyl alcohol, glycerol monostearate, aluminium stearate, bentonite, celluloses, liquid triglycerides, paraffins, highly disperse silica or kieselguhr, calcium carbonate, magnesium oxide, antioxidants (for example tocopherols, butylhydroxy toluene, ascorbyl palmitate, propyl gallate), preservatives and dye.

In one preferred embodiment, the compositions of the invention for suppository bases contain 90 to 99.8% by weight of a glycerol fatty acid ester and 0.2 to 10% by weight of an adduct of 5 to 50 mols of ethylene oxide with 1 mol of hardened castor oil.

Compositions of the invention for suppository bases which have a so-called elevation melting point of 29° to 45° C. are particularly preferred.

The compositions of the invention for suppository bases are particularly suitable for the preparation of water-containing suppositories, i.e. for the incorporation of active principles which are only available or processible in aqueous solution. Active principles such as these may be processed with the compositions of the invention for suppository bases in such quantities that the suppositories obtained contain up to 30% by weight water in homogeneous distribution, i.e. homogeneous dispersion.

Accordingly, the present invention relates particularly to water-containing suppositories which contain 70 to 99.5% by weight of the composition of the invention for suppository bases and 0.5 to 30% by weight of water homogeneously dispersed therein. Suppositories such as these are distinguished by high homogeneity, by high fracture resistance and by high compatibility with mucous membrane.

The following Examples are intended to illustrate but not limit the invention.

EXAMPLES

1. Preparation of compositions of the invention for suppository bases

| 1.1 Novata ®BC | 987.8 g |
|---|---|
| Hydrogenated castor oil + 40 mol EO | 12.2 g |
| | 1000.0 g |

The constituents were melted and homogenized together at around 50° C. Homogeneous compositions having an elevation melting point of 34.4° C. were obtained after cooling to 20° C.

| 1.2 Novata ®BC | 951.2 g |
|---|---|
| Hydrogenated castor oil + 7 mol EO | 48.8 g |
| | 1000.0 g |

Preparation was carried out as in Example 1. A homogeneous composition having an elevation melting point of 34.2° C. was obtained.

| 1.3 Novata ®A | 977.8 g |
|---|---|
| Hydrogenated castor oil + 7 mol EO | 22.2 g |
| | 1000.0 g |

Preparation was carried out as in Example 1. A homogeneous composition having an elevation melting point of 34.2° C. was obtained.

The following commercial products were used:

Novata ® A and Novata ® BC (Henkel KGaA, Düsseldorf), which are mixtures of triglycerides containing small proportions of di- and monoglycerides and of a $C_{12}$–$C_{18}$ fatty acid cut.

| Characteristics | Novata A | Novata BC |
|---|---|---|
| Elevation melting point | 33.5–35.5° C. | 33.5–35.5° C. |
| Solidification point | 29–31° C. | 30.5–32.5° C. |
| Acid value | below 0.3 | below 0.3 |
| Saponification value | 225–240 | 225–240 |
| Hydroxyl value | 35–45 | 30–40 |

2. Preparation of suppositories

| 2.1 Suppository base of Example 1.1 | 82 g |
|---|---|
| Aqueous suspension of the corpuscular constituents and metabolism products of 1700 million *Escherichia coli* and 17 mg phenol per g suspension | 18 g |
| | 100 g |

Preparation:

The suppository base was melted at 50° C. After cooling to 38° C., the active-principle suspension was added and homogeneously distributed in the melt. After cooling to around 33° C., the homogeneous dispersion was poured into the suppository mold and removed after 1 hour at 20° C. Homogeneous suppositories weighing approx. 2.15 g were obtained.

| 2.2 Suppository base of Example 1.2 | 82 g |
|---|---|
| Aqueous suspension of Example 2.1 | 18 g |
| | 100 g |

The suppositories were prepared in the same way as in Example 2.1

| 2.3 Suppository base of Example 1.3 | 82.0 g |
|---|---|
| Glycerol, 86% | 15.0 g |
| Lactose | 1.5 g |
| Extractum Belladonna | 1.5 g |
| | 100.0 g |

Preparation:

The suppository base was melted at 50° C. After cooling to 38° C., glycerol, lactose and Extractum Belladonna were added and homogeneously distributed in the melt. After cooling to 33° C., the homogeneous dispersion was poured into the suppository mold and removed after 1 hour at 20° C. Homogeneous suppositories weighing approx. 2.15 g were obtained.

I claim:

1. In a composition for a suppository base consisting essentially of water insoluble fat and an emulsifier, the improvement wherein the emulsifier is an adduct of from about 5 to about 50 moles of ethylene oxide per mole of hardened castor oil.

2. The composition of claim 1 wherein from about 0.1 to about 20% by weight of the emulsifier is present therein.

3. The composition of claim 1 wherein the water-insoluble fat is a glycerol fatty acid ester.

4. The composition of claim 2 wherein the water-insoluble fat is a glycerol fatty acid ester.

5. The composition of claim 1 wherein the composition has an elevation melting point of from about 29° to about 45° C.

6. A suppository base composition consisting essentially of from about 90 to about 99.8% by weight of at least one water-insoluble fat and from about 0.2 to about 10% by weight of an adduct of from about 5 to about 50 mols of ethylene oxide with 1 mol of hardened castor oil.

7. The composition of claim 6 wherein the composition has an elevation melting point of from about 29° to about 45° C.

8. The composition of claim 6 wherein the at least one water-insoluble fat is a glycerol fatty acid ester.

9. A water-containing suppository composition comprising from about 70 to about 99.5% by weight of the suppository base of claim 1 and from about 0.5 to about 30% by weight of water homogeneously dispersed therein.

10. A water-containing suppository composition comprising from about 70 to about 99.5% by weight of the suppository base of claim 3 and from about 0.5 to about 30% by weight of water homogeneously dispersed therein.

11. A water-containing suppository composition comprising from about 70 to about 99.5% by weight of the suppository base of claim 6 and from about 0.5 to about 30% by weight of water homogeneously dispersed therein.

12. A water-containing suppository composition comprising from about 70 to about 99.5% by weight of the suppository base of claim 8 and from about 0.5 to about 30% by weight of water homogeneously dispersed therein.

* * * * *